United States Patent [19]

Mills

[11] Patent Number: 5,031,605

[45] Date of Patent: Jul. 16, 1991

[54] MEDICAL GIN POLE

[76] Inventor: Michael Mills, 1803 Liberty Ave., Richmond, Ind. 47374

[21] Appl. No.: 417,433

[22] Filed: Oct. 5, 1989

[51] Int. Cl.[5] .................... A61F 5/00

[52] U.S. Cl. .................... 128/68; 272/126; 272/900

[58] Field of Search .................... 272/900, 903, 94, 96, 272/116, 126, 131, 133, 136, 143, 61, 62, 93, 113; 128/68, 25 R, 25 B

[56] References Cited

U.S. PATENT DOCUMENTS

| | | | |
|---|---|---|---|
| 715,520 | 12/1902 | Wallace | 272/62 |
| 1,410,149 | 3/1922 | Williams | 272/62 |
| 1,856,785 | 5/1932 | Phillips . | |
| 2,274,574 | 2/1942 | Zerne | 128/25 R |
| 2,305,548 | 12/1942 | Nichols | 272/126 |
| 2,919,134 | 12/1959 | Zuro | 272/62 X |
| 3,072,400 | 1/1963 | Dykinga | 128/25 R |
| 3,077,613 | 2/1963 | Mayer | 272/900 X |
| 3,141,670 | 7/1964 | Smyrni et al. | 272/113 X |
| 3,392,410 | 7/1968 | Grahn . | |
| 3,483,999 | 12/1969 | Barrett | 272/62 |
| 3,683,898 | 8/1972 | Underwood | 128/25 R |
| 3,877,421 | 4/1975 | Brown | 128/25 R |
| 4,003,479 | 1/1977 | Reyer . | |
| 4,153,244 | 5/1979 | Tauber, Jr. | 272/94 X |
| 4,252,063 | 2/1981 | Brooks, Jr. | 128/25 R X |
| 4,253,207 | 3/1981 | Marcyan | 128/25 R X |
| 4,256,300 | 3/1981 | Boucher | 272/113 X |
| 4,355,633 | 10/1982 | Heilbrum | 128/25 R |
| 4,375,707 | 3/1983 | Boerigter . | |
| 4,446,587 | 5/1984 | Jump . | |
| 4,531,514 | 7/1985 | McDonald et al. | 272/143 X |
| 4,602,618 | 7/1986 | Berzé128 | 25 B X/ |
| 4,666,151 | 5/1987 | Chillier | 272/136 X |

*Primary Examiner*—Robert Bahr
*Assistant Examiner*—Linda C. M. Dvorak
*Attorney, Agent, or Firm*—Jerry T. Kearns

[57] ABSTRACT

A medical gin pole for use by patients in performing physical therapy has a collapsible construction to enable convenient portability. In an erected condition, the gin pole has an A-frame configuration formed by an elongated rectangular base and a pair of struts. Lower ends of each of the struts are frictionally engaged in spaced apertures formed in the base. Upper ends of each of the struts are pivotally mounted to a bracket. A folding brace extends between the struts and serves to retain the struts in an erected condition. A linear guide rod is pivotally mounted to the bracket for movement about a pivot axis perpendicular to the pivot axes of the strut. The linear guide rod may be extensible and terminates in a mounting plate for securement to a vertical wall surface. A carriage is formed by a hollow sleeve surrounding the rod. The carriage is mounted for reciprocal movement along the linear guide rod and a pulley is suspended therefrom. A manipulating mechanism is supported by the pulley for selectively raising and lowering limbs of a patient.

1 Claim, 4 Drawing Sheets

Fig. 7
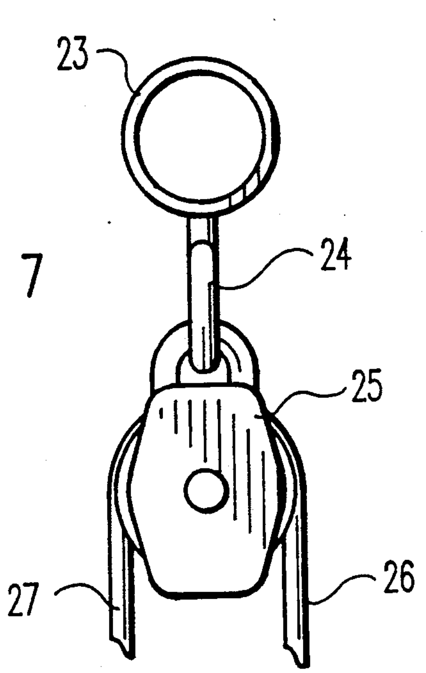
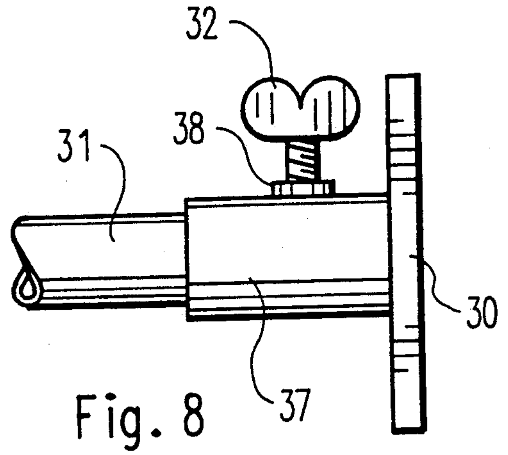
Fig. 8
Fig. 10
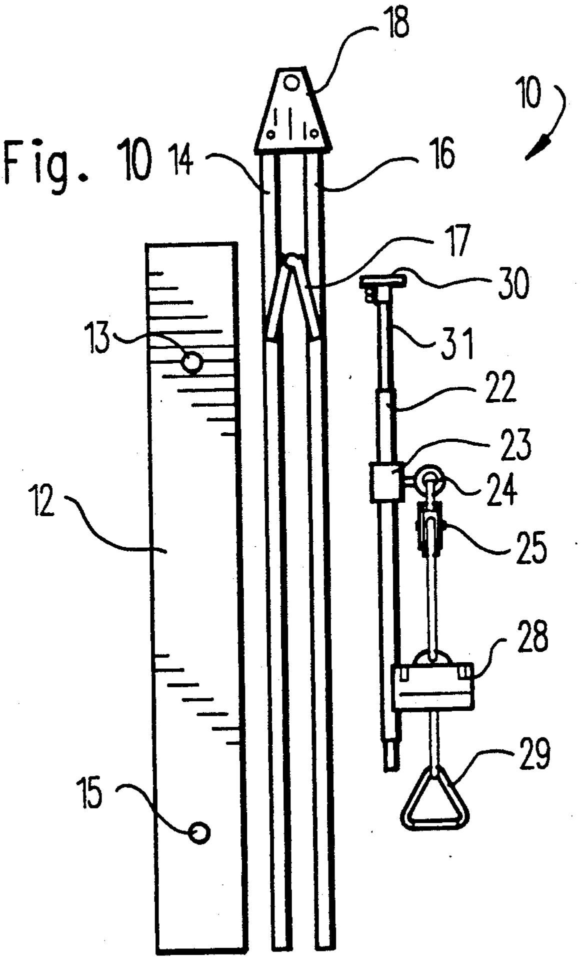
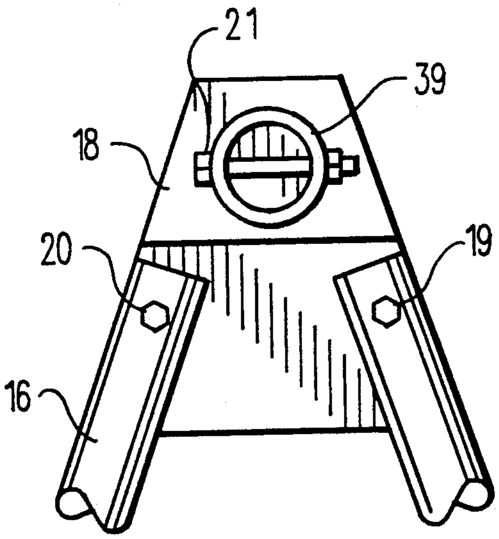
Fig. 9

MEDICAL GIN POLE

BACKGROUND OF THE INVENTION

1. Field of the Invention

The present invention relates to physical therapy devices, and more particularly pertains to a medical gin pole for enabling patients to perform physical therapy at home. Many individuals recovering from strokes, accidents, and other debilitating physical conditions require physical therapy to maintain and improve muscular and neural conditions. Additionally, protracted inactivity results in the atrophy of various muscle groups and the calcification of joints such as shoulders, elbows and knees. In order to overcome these problems, the present invention provides an inexpensive, convenient and easily portable physical therapy device.

2. Description of the Prior Art

Various types of physical therapy devices are known in the prior art. A typical example of such a physical therapy device is to be found in E. Phillips U.S. Pat. No. 1,856,785, issued on May 3, 1932. This patent discloses an invalid bed construction which incorporates a plurality of pivotal arms for manipulating patient supporting slings. G. Grahn U.S. Pat. No. 3,392,410, issued on July 16, 1968, discloses a patient stretcher including a patient lifting mechanism. W. Reyer U.S. Pat. No. 4,003,479, issued on Jan. 18, 1977, discloses a hoist and transporting apparatus for lifting and moving disabled persons from a bed to a chair. The device has a frame structure including an overhead support deck and a rotatably mounted boom carrier. M. Boerigter U.S. Pat. No. 4,375,707, issued on Mar. 8, 1983, discloses an invalid bed including a frame and an overhead support structure which provides an elevated diagonally extending support surface for a pivot arm. C. Jump U.S. Pat. No. 4,446,587, issued on May 8, 1984, discloses a patient positioning device for a bed including a horizontal support beam, a pair of motors coupled to the support beam, and cable and hook assemblies associated with the motors for selectively lifting portions of a patient's body from a bed.

While the above mentioned devices are directed to physical therapy and invalid lifting devices, none of these prior patents disclose a medical gin pole which is collapsible for convenient transportation to enable patients to perform physical therapy in a home environment. Inasmuch as the art is relatively crowded with respect to these various types of physical therapy devices, it can be appreciated that there is a continuing need for and interest in improvements to such physical therapy devices, and in this respect, the present invention addresses this need and interest.

SUMMARY OF THE INVENTION

In view of the foregoing disadvantages inherent in the known types of physical therapy devices now present in the prior art, the present invention provides an improved medical gin pole. As such, the general purpose of the present invention, which will be described subsequently in greater detail, is to provide a new and improved medical gin pole which has all the advantages of the prior art physical therapy devices and none of the disadvantages.

To attain this, a representative embodiment of the concepts of the present invention is illustrated in the drawings and makes use of a medical gin pole for use by patients in performing physical therapy which has a collapsible construction to enable convenient portability. In an erected condition, the gin pole has an A-frame configuration formed by an elongated rectangular base and a pair of struts. Lower ends of each of the struts are frictionally engaged in spaced apertures formed in the base. Upper ends of each of the struts are pivotally mounted to a bracket. A folding brace extends between the struts and serves to retain the struts in an erected condition. A linear guide rod is pivotally mounted to the bracket for movement about a pivot axis perpendicular to the pivot axes of the strut. The linear guide rod may be extensible and terminates in a mounting plate for securement to a vertical wall surface. A carriage is formed by a hollow sleeve surrounding the rod. The carriage is mounted for reciprocal movement along the linear guide rod and a pulley is suspended therefrom. A manipulating mechanism is supported by the pulley for selectively raising and lowering limbs of a patient.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the public generally, and especially those who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved medical gin pole which has all the advantages of the prior art physical therapy devices and none of the disadvantages.

It is another object of the present invention to provide a new and improved medical gin pole which may be easily and efficiently manufactured and marketed.

It is a further object of the present invention to provide a new and improved medical gin pole which is of a durable and reliable construction.

An even further object of the present invention is to provide a new and improved medical gin pole which is susceptible of a low cost of manufacture with regard to both materials and labor, and which accordingly is then susceptible of low prices of sale to the consuming public, thereby making such physical therapy devices economically available to the buying public.

Still yet another object of the present invention is to provide a new and improved medical gin pole which provides in the apparatuses and methods of the prior art some of the advantages thereof, while simultaneously overcoming some of the disadvantages normally associated therewith.

Still another object of the present invention is to provide a new and improved medical gin pole which is collapsible for convenient transportation.

Yet another object of the present invention is to provide a new and improved medical gin pole for enabling patients to perform physical therapy in a home environment.

Even still another object of the present invention is to provide a new and improved medical gin pole adaptable for manipulating various limbs of a patient to promote muscular and neural conditioning.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 7 is a detail view illustrating the construction of the reciprocal carriage mechanism.

FIG. 8 is a detail view illustrating the linear guide member wall securement mounting plate.

FIG. 9 is a detail view illustrating the construction of the pivotal frame brace.

FIG. 10 illustrates the medical gin pole of the present invention in a disassembled condition.

DESCRIPTION OF THE PREFERRED EMBODIMENT

Figure 1:
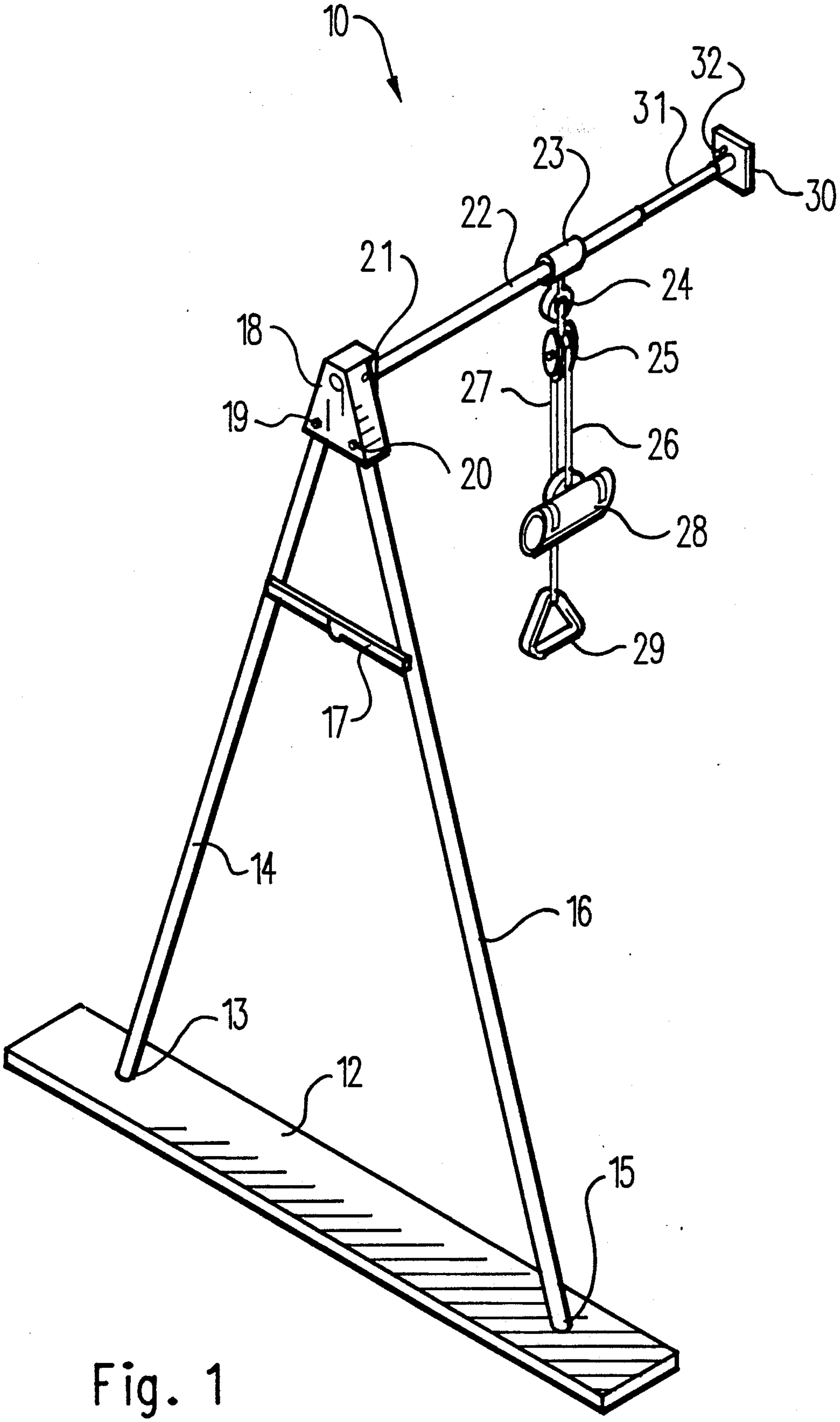
FIG. 1 is a perspective view of the medical gin pole according to the present invention.

With reference now to the drawings, and in particular to FIG. 1 thereof, a new and improved medical gin pole embodying the principles and concepts of the present invention and generally designated by the reference numeral 10 will be described.

More specifically, it will be noted that the first embodiment 10 of the invention includes a base 12, which may be in the form of an elongated rectangular wooden board. A pair of spaced apertures 13 and 15 are formed in the base 12 and are dimensioned for frictional engagement with bottom ends of a pair of struts 14 and 16. The struts 14 and 16 are preferably formed from elongated cylindrical rods. Upper ends of each of the struts 14 and 16 are pivotally secured by pivot bolts 19 and 20 to a bracket 18. The struts 14 and 16 in the base 12 form an A-frame configuration. A folding brace 17 extends between the struts 14 and 16 and serve to maintain the illustrated erected configuration. A pivot mounting bolt 21 extends perpendicularly to the strut pivot mounting bolts 19 and 20, and pivotally secures a first end of a linear guide member 22 to the bracket 18. The linear guide member 22 is formed by an elongated cylindrical rod and may include a telescopically extensible portion 31. The end of the linear guide member 22 opposite the bracket 18 terminates in a wall engaging mounting plate 30 adapted for securement through conventional threaded fasteners to a vertical wall surface. The mounting plate 30 may include a set screw 30 for selective engagement with the distal end portion of the extension member 31. A carriage 23 is formed by a hollow cylindrical sleeve mounted for reciprocal movement along the rod 22. An eye bolt 24 extends downwardly from the carriage 23 and serves to suspend a pulley 25. Opposite ends 26 and 27 of a nYlon rope extend from the pulley 25. A limb engaging padded support member 28 is secured to the rope portion 26 and a handle 29 is secured to the opposite rope portion 27.

Figure 2:
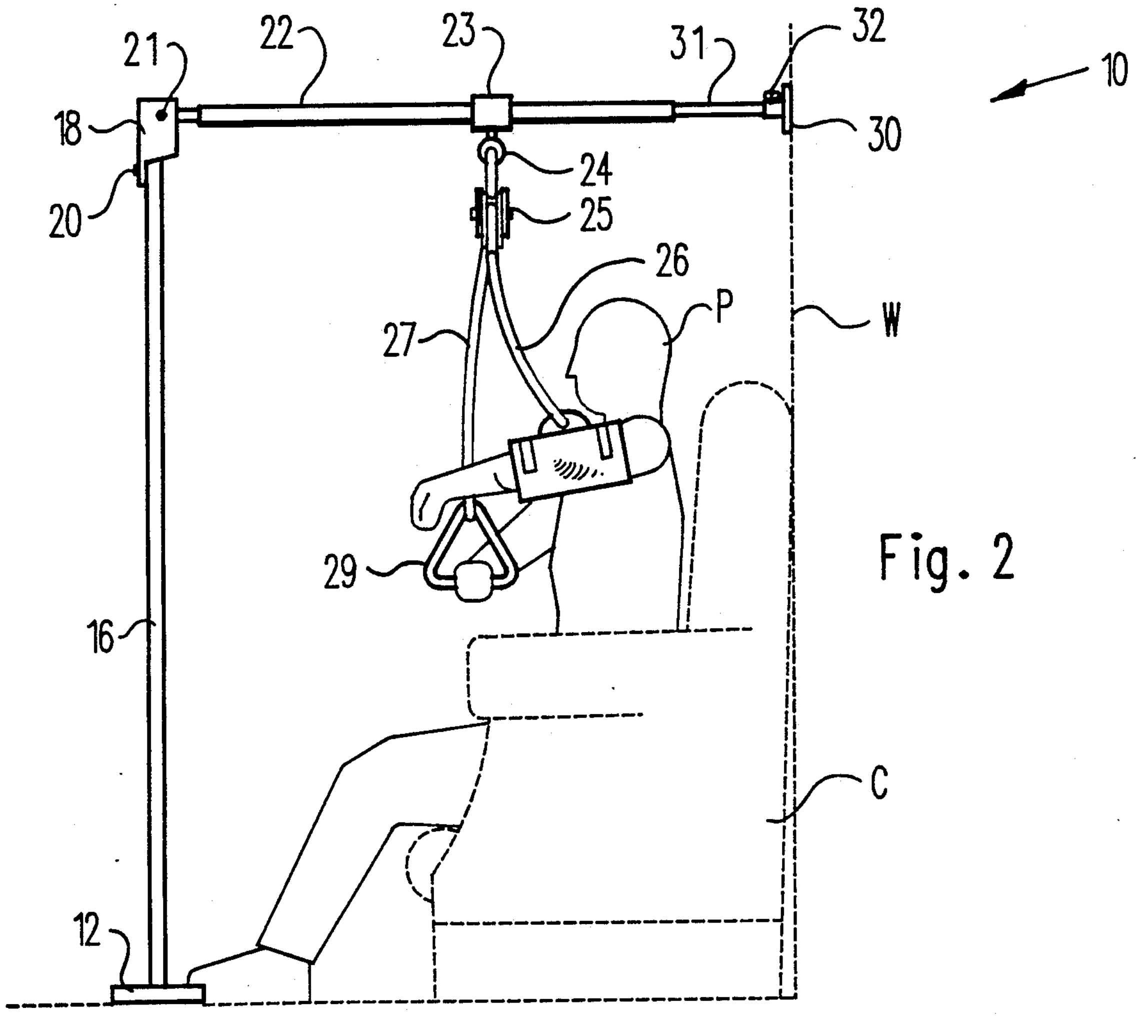
FIG. 2 is a side view illustrating the manner of use of the medical gin pole of the present invention.

As shown in FIG. 2, the padded support member 28 is secured around the limb of a patient P and the handle 29 is then selectively raised and lowered to perform physical therapy on the selected limb. The patient P may remain comfortably seated in a chair C adjacent a vertical wall surface W to which the mounting plate 30 is secured. The extensible construction 31 of the linear guide member 22 enables convenient adaptation of the device depending upon patient size and other physical room environment consideration.

Figure 3:
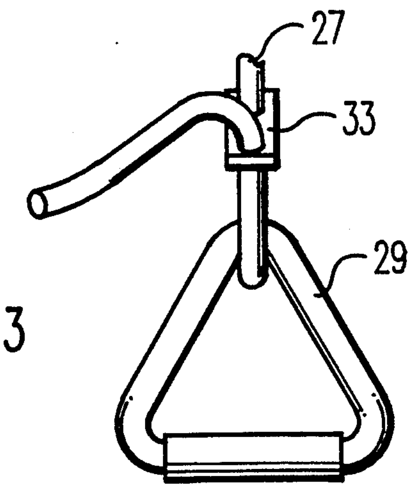
FIG. 3 is a detail view illustrating an adjustable mounting for a limb manipulating handle.

FIG. 3 illustrates an example construction for securing the handle 29 to the rope 27. A slide fastener 33 is provided with a pair of spaced apertures through which the rope 27 is received. This provides a frictional clamp type securement which allows convenient adjustment of the position of the handle 29 to accommodate various different patients and allow adaptation for use with various different limbs.

Figure 4:
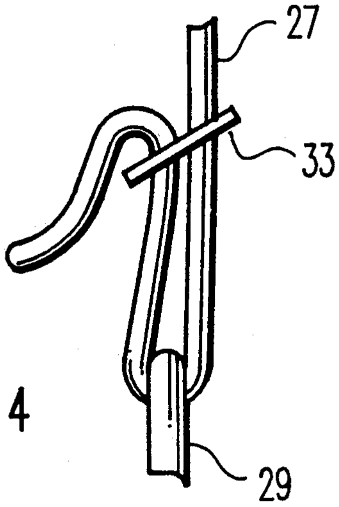
FIG. 4 is side view of the handle attachment mechanism of FIG. 3.

FIG. 4 further illustrates the adjustable handle securing construction of FIG. 3.

Figure 5:
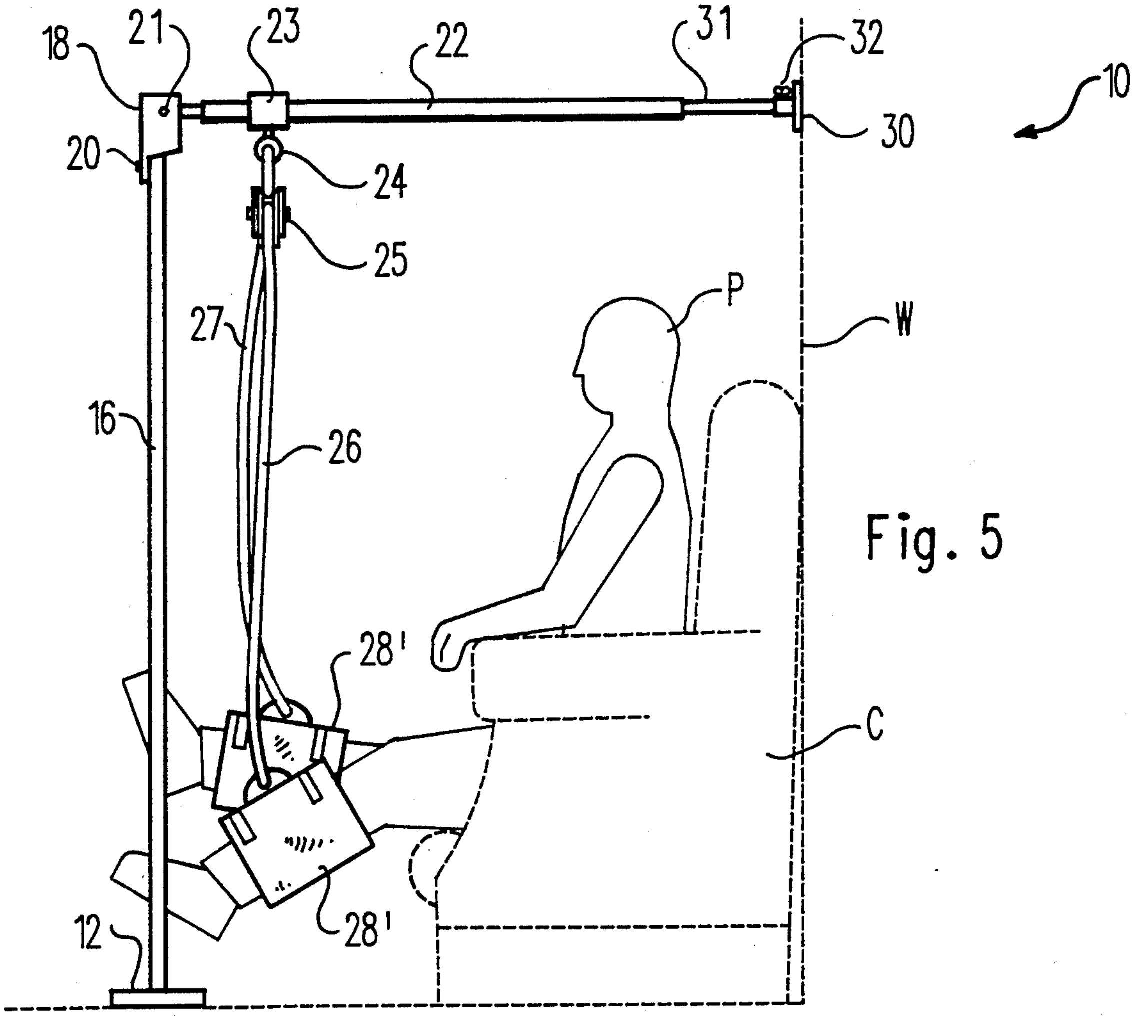
FIG. 5 is a side view illustrating an alternative manner of utilizing the medical gin pole of the present invention.

FIG. 5 illustrate the medical gin pole 10 of the present invention, provided with a pair of padded support members 28' dimensioned for engagement around the legs of a patient P. This allows the patient P to alternately raise and lower their legs.

Figure 6:
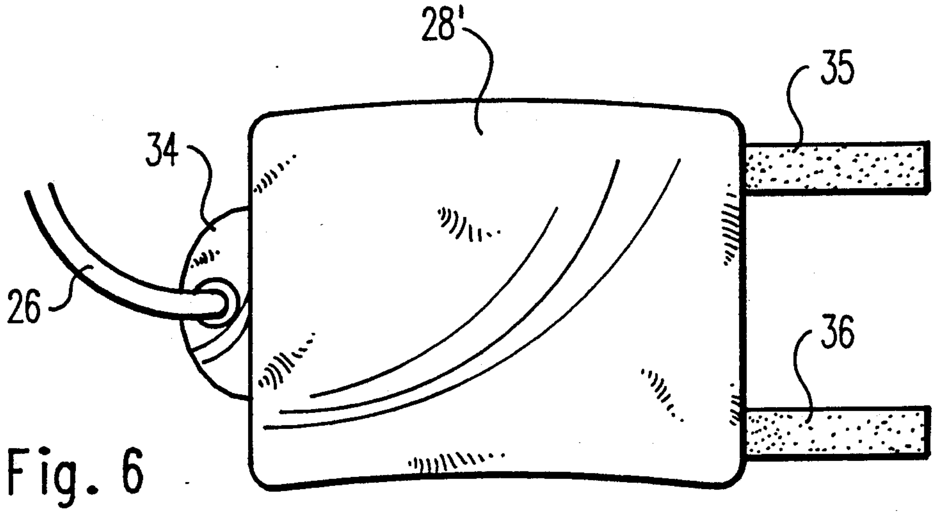
FIG. 6 is a detail view illustrating the construction of a limb engaging padded support member.

As shown in FIG. 6, the limb engaging support member 28' includes a tab portion 34 to which the pulley rope end 26 is secured. Additionally, a pair of hook and loop type fastening strips 35 and 36 are provided for securing the support member 28' around a selected limb. The fastening strips 35 and 36 are preferably of the type sold under the trademark VELCRO.

FIG. 7 is a detail view which illustrates the construction of the carriage mechanism. The carriage 23 is in the form of a hollow cylindrical sleeve and includes a downwardly depending eye bolt 24 to which the pulley 25 is attached.

FIG. 8 is a detail view illustrating the construction of the linear guide member wall securement plate. The plate 30 may be secured to a vertical wall surface utilizing nails or threaded fasteners. The mounting plate 30 includes a perpendicularly extending cylindrical socket 37 dimensioned to receive the distal end portion of the linear guide member extension member 31. A set screw 32 is threadably engaged with a threaded boss 38 communicating with the interior of the socket 37. Thus, the extension member end portion may be released by loosening the set screw 32. By providing a plurality of wall mounting plates 30 in different locations, the medical gin pole of the present invention may be regularly transported between these locations.

FIG. 9 is a detail view which illustrates the construction of the bracket 18. The struts 14 and 16 are mounted for movement about parallel pivot axis by bolts 19 and 20. A socket 39 which receives an end portion of the linear guide member 22 is mounted for pivotal movement by a bolt 21, which extends perpendicularly to the bolts 19 and 20.

As shown in FIG. 10, the medical gin pole of the present invention may be quickly disassembled to a compact size for packaging and transportation purposes. Although illustrated detached from the bracket 18, it is contemplated that the linear guide member 22 may remain secured to the bracket 18, to form a collapsed tripod configuration.

As may now be understood, the present invention provides an inexpensive and easily transportable device which enables patients and assisting individuals to conveniently perform physical therapy in a home environment. Through a relatively small amount of training and the proper use of this device, many patients may be afforded a level of care previously unavailable due to the inordinate expense of professional physical therapy.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A medical gin pole, comprising:

a generally horizontally extending elongated base;

a pair of spaced apertures formed in said base;

a pair of strut members each having a first end frictionally engageable in one of said apertures;

a bracket;

a second end of each of said strut members pivotally mounted on said bracket;

said base and said struts forming an A-frame configuration;

a brace having a central folding joint extending between said struts for retaining said struts in an erected condition;

an elongated telescopically extensible, generally horizontally extending rod having a first end pivotally mounted on said bracket, said elongated rod mounted for movement about a pivot axis perpendicular to pivot axes of said struts;

mounting means for securing a second end of said elongated rod to a vertical wall surface;

a hollow sleeve surrounding said elongated rod and mounted for reciprocal movement along said elongated rod;

a pulley suspended from said sleeve;

and manipulating means mounted on said pulley for moving limbs of a patient during physical therapy.

* * * * *